US009155578B2

(12) United States Patent
Chegini et al.

(10) Patent No.: US 9,155,578 B2
(45) Date of Patent: Oct. 13, 2015

(54) EXPANDABLE FASTENER

(75) Inventors: Salman Chegini, Oberdorf (CH); Andreas Gfeller, Oberdorf (CH); Jacques Teisen, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 152 days.

(21) Appl. No.: 13/406,928

(22) Filed: Feb. 28, 2012

(65) Prior Publication Data
US 2013/0226251 A1 Aug. 29, 2013

(51) Int. Cl.
*A61B 17/84* (2006.01)
*A61B 17/86* (2006.01)

(52) U.S. Cl.
CPC ............. *A61B 17/844* (2013.01); *A61B 17/864* (2013.01); *A61B 17/8625* (2013.01); *A61B 17/8685* (2013.01); *A61B 17/869* (2013.01); *A61B 2017/8655* (2013.01)

(58) Field of Classification Search
CPC ..................... A61B 2017/8655; A61B 17/869; A61B 17/844
USPC ........................................................ 606/313
See application file for complete search history.

(56) References Cited

U.S. PATENT DOCUMENTS

| 1,438,648 | A | 12/1922 | Jacobs |
| 1,788,270 | A | 1/1931 | Baranoff |
| 2,913,953 | A | 11/1959 | Tendler |
| 3,030,951 | A | 4/1962 | Mandarino |
| 3,343,263 | A | 9/1967 | Henlotter |
| 3,867,728 | A | 2/1975 | Stubstad et al. |
| 3,875,595 | A | 4/1975 | Froning |
| 3,896,504 | A | 7/1975 | Fischer |
| 4,204,531 | A | 5/1980 | Aginsky |
| 4,313,434 | A | 2/1982 | Segal |

(Continued)

FOREIGN PATENT DOCUMENTS

| DE | 2558584 | 7/1977 |
| EP | 0105829 | 4/1984 |

(Continued)

OTHER PUBLICATIONS

Expanding Orthopedics, "XPED Pedicle Screw System™", http://www.xortho.com/xped-pedicle-screw-system%E2%84%A2 (2011).

(Continued)

*Primary Examiner* — David Bates
(74) *Attorney, Agent, or Firm* — Meunier Carlin & Curfman LLC

(57) ABSTRACT

Implementations of the present disclosure provide a fastener including a tip portion, a proximal portion, an advancement mechanism and an expandable member. The tip portion has a first surface. The proximal portion is configured for coupling to the tip portion and has a second surface. The mechanism advances the first surface toward the second surface. The expandable member includes a first end abutting the first surface of the tip portion and a second end abutting the second surface of the proximal portion. Advancement of the two surfaces toward each other advances the first end of the expandable member toward the second end of the expandable member. The expandable member is configured to expand in response to the advancement. At least one of the ends of the expandable member is a free end extending under and configured to rotate with respect to an abutting one of the first or second surfaces.

38 Claims, 8 Drawing Sheets

(56) References Cited

U.S. PATENT DOCUMENTS

| | | |
|---|---|---|
| 4,472,088 A | 9/1984 | Martin |
| 4,655,777 A | 4/1987 | Dunn et al. |
| 4,684,370 A | 8/1987 | Barrett |
| 4,686,973 A | 8/1987 | Frisch |
| 4,733,665 A | 3/1988 | Palmaz |
| 4,735,625 A | 4/1988 | Davidson |
| 4,755,184 A | 7/1988 | Silverberg |
| 4,772,287 A | 9/1988 | Ray et al. |
| 4,854,312 A | 8/1989 | Raftopoulos et al. |
| 4,863,477 A | 9/1989 | Monson |
| 4,888,024 A | 12/1989 | Powder |
| 4,904,260 A | 2/1990 | Ray et al. |
| 4,906,190 A | 3/1990 | Michna |
| 4,932,969 A | 6/1990 | Frey et al. |
| 4,932,975 A | 6/1990 | Main et al. |
| 4,936,848 A | 6/1990 | Bagby |
| 4,969,888 A | 11/1990 | Scholten et al. |
| 4,976,725 A | 12/1990 | Chin et al. |
| 5,015,247 A | 5/1991 | Michelson |
| 5,015,255 A | 5/1991 | Kuslich |
| 5,030,233 A | 7/1991 | Ducheyne |
| 5,037,445 A | 8/1991 | Sander et al. |
| 5,047,055 A | 9/1991 | Bao et al. |
| 5,053,035 A | 10/1991 | McLaren |
| 5,059,193 A | 10/1991 | Kuslich |
| 5,071,435 A | 12/1991 | Fuchs et al. |
| 5,102,413 A | 4/1992 | Poddar |
| 5,108,404 A | 4/1992 | Scholten et al. |
| 5,108,438 A | 4/1992 | Stone |
| 5,116,305 A | 5/1992 | Milder et al. |
| 5,133,767 A | 7/1992 | Frey et al. |
| 5,147,359 A | 9/1992 | Cozad et al. |
| 5,147,360 A | 9/1992 | Dubousset |
| 5,154,718 A | 10/1992 | Cozad et al. |
| 5,171,280 A | 12/1992 | Baumgartner |
| 5,171,281 A | 12/1992 | Parsons et al. |
| 5,176,678 A | 1/1993 | Tsou |
| 5,176,680 A | 1/1993 | Vignaud et al. |
| 5,176,692 A | 1/1993 | Wilk et al. |
| 5,190,543 A | 3/1993 | Schlapfer |
| 5,192,326 A | 3/1993 | Bao et al. |
| 5,207,678 A | 5/1993 | Harms et al. |
| 5,209,753 A | 5/1993 | Biedermann et al. |
| 5,261,907 A | 11/1993 | Vignaud et al. |
| 5,261,913 A | 11/1993 | Marnay |
| 5,263,931 A | 11/1993 | Miller |
| 5,275,600 A | 1/1994 | Allard et al. |
| 5,275,622 A | 1/1994 | Lazarus et al. |
| 5,282,801 A | 2/1994 | Sherman |
| 5,282,863 A | 2/1994 | Burton |
| 5,303,718 A | 4/1994 | Krajicek |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,306,311 A | 4/1994 | Stone et al. |
| 5,314,477 A | 5/1994 | Marnay |
| 5,314,478 A | 5/1994 | Oka et al. |
| 5,331,975 A | 7/1994 | Bonutti |
| 5,342,298 A | 8/1994 | Michaels et al. |
| 5,350,379 A | 9/1994 | Spievack |
| 5,376,123 A | 12/1994 | Klau et al. |
| 5,390,683 A | 2/1995 | Pisharodi |
| 5,437,834 A | 8/1995 | Okimatsu et al. |
| 5,474,563 A | 12/1995 | Myler et al. |
| 5,503,164 A | 4/1996 | Friedman |
| 5,549,679 A | 8/1996 | Kuslich |
| 5,556,429 A | 9/1996 | Felt |
| 5,562,704 A | 10/1996 | Tamminmäki et al. |
| 5,571,189 A | 11/1996 | Kuslich |
| 5,599,301 A | 2/1997 | Jacobs et al. |
| 5,601,593 A | 2/1997 | Freitag |
| 5,626,581 A | 5/1997 | Staehlin et al. |
| 5,674,295 A | 10/1997 | Ray et al. |
| 5,707,390 A | 1/1998 | Bunutti |
| 5,716,416 A | 2/1998 | Lin |
| 5,725,541 A | 3/1998 | Anspach, III et al. |
| 5,749,888 A | 5/1998 | Yock |
| 5,788,703 A | 8/1998 | Mittelmeier et al. |
| 5,827,289 A | 10/1998 | Reiley et al. |
| 5,888,220 A | 3/1999 | Felt et al. |
| 5,893,850 A | 4/1999 | Cachia |
| 5,961,554 A | 10/1999 | Janson et al. |
| 5,972,015 A | 10/1999 | Scribner et al. |
| 5,989,290 A | 11/1999 | Biedermann et al. |
| 6,015,436 A | 1/2000 | Schonhoffer |
| 6,022,376 A | 2/2000 | Assell et al. |
| 6,025,537 A | 2/2000 | Werding et al. |
| 6,066,154 A | 5/2000 | Reiley et al. |
| 6,127,597 A | 10/2000 | Beyar et al. |
| 6,129,763 A | 10/2000 | Chauvin et al. |
| 6,149,651 A | 11/2000 | Drewry et al. |
| 6,174,334 B1 | 1/2001 | Suddaby |
| 6,176,882 B1 | 1/2001 | Biedermann et al. |
| 6,183,503 B1 | 2/2001 | Hart et al. |
| 6,183,518 B1 | 2/2001 | Ross et al. |
| 6,187,048 B1 | 2/2001 | Milner et al. |
| 6,213,775 B1 | 4/2001 | Reipur |
| 6,224,630 B1 | 5/2001 | Bao et al. |
| 6,241,734 B1 | 6/2001 | Scribner et al. |
| 6,245,107 B1 | 6/2001 | Ferree |
| 6,248,110 B1 | 6/2001 | Reiley et al. |
| 6,248,131 B1 | 6/2001 | Felt et al. |
| 6,261,289 B1 | 7/2001 | Levi |
| 6,273,655 B1 | 8/2001 | McAlpine et al. |
| 6,293,743 B1 * | 9/2001 | Ernst et al. ............. 411/24 |
| 6,306,177 B1 | 10/2001 | Felt et al. |
| 6,319,255 B1 | 11/2001 | Grundei et al. |
| 6,328,758 B1 | 12/2001 | Tornier et al. |
| 6,383,190 B1 | 5/2002 | Preissman |
| 6,395,032 B1 | 5/2002 | Gauchet |
| 6,425,923 B1 | 7/2002 | Stalcup et al. |
| 6,428,576 B1 | 8/2002 | Haldimann |
| 6,443,988 B2 | 9/2002 | Felt et al. |
| 6,447,515 B1 | 9/2002 | Meldrum |
| 6,478,800 B1 | 11/2002 | Fraset et al. |
| 6,482,235 B1 | 11/2002 | Lambrecht et al. |
| 6,508,839 B1 | 1/2003 | Lambrecht et al. |
| 6,554,833 B2 | 4/2003 | Levy et al. |
| 6,582,471 B1 | 6/2003 | Bittmann et al. |
| 6,592,625 B2 | 7/2003 | Cauthen |
| 6,648,893 B2 | 11/2003 | Dudasik |
| 6,852,095 B1 | 2/2005 | Ray |
| 6,869,445 B1 | 3/2005 | Johnson |
| 7,153,306 B2 | 12/2006 | Ralph et al. |
| 7,491,236 B2 * | 2/2009 | Cragg et al. ............. 623/17.11 |
| 7,520,883 B2 * | 4/2009 | Manzo ............. 606/153 |
| 7,547,324 B2 | 6/2009 | Cragg et al. |
| 7,645,279 B1 | 1/2010 | Haupt |
| 7,662,173 B2 | 2/2010 | Cragg et al. |
| 8,388,660 B1 * | 3/2013 | Abdou ............. 606/267 |
| 8,591,582 B2 * | 11/2013 | Anderson et al. ......... 623/16.11 |
| 2001/0000186 A1 | 4/2001 | Bramlet et al. |
| 2001/0011174 A1 | 8/2001 | Reiley et al. |
| 2002/0045942 A1 | 4/2002 | Ham |
| 2002/0049447 A1 | 4/2002 | Li |
| 2002/0068939 A1 | 6/2002 | Levy et al. |
| 2002/0068974 A1 | 6/2002 | Kuslich et al. |
| 2002/0156531 A1 | 10/2002 | Felt et al. |
| 2002/0165544 A1 * | 11/2002 | Perren et al. ............. 606/63 |
| 2002/0177866 A1 | 11/2002 | Weikel et al. |
| 2002/0198527 A1 | 12/2002 | Muckter |
| 2003/0033017 A1 | 2/2003 | Lotz et al. |
| 2003/0088249 A1 | 5/2003 | Furderer |
| 2003/0220649 A1 | 11/2003 | Bao et al. |
| 2004/0073308 A1 | 4/2004 | Kuslich et al. |
| 2004/0097930 A1 | 5/2004 | Justis et al. |
| 2004/0122431 A1 * | 6/2004 | Biedermann et al. ............. 606/73 |
| 2005/0065526 A1 | 3/2005 | Drew |
| 2005/0113929 A1 | 5/2005 | Cragg et al. |
| 2005/0159749 A1 | 7/2005 | Levy et al. |
| 2005/0187555 A1 | 8/2005 | Biedermann et al. |
| 2005/0234498 A1 | 10/2005 | Gronemeyer et al. |
| 2006/0100706 A1 | 5/2006 | Shadduck et al. |

(56) References Cited

U.S. PATENT DOCUMENTS

| | | | |
|---|---|---|---|
| 2007/0038219 A1 | 2/2007 | Matthis et al. | |
| 2007/0093899 A1 | 4/2007 | Dutoit et al. | |
| 2007/0198018 A1 | 8/2007 | Biedermann et al. | |
| 2008/0221623 A1* | 9/2008 | Gooch | 606/302 |
| 2008/0288003 A1* | 11/2008 | McKinley | 606/313 |
| 2008/0294204 A1 | 11/2008 | Chirico et al. | |
| 2009/0125028 A1* | 5/2009 | Teisen et al. | 606/63 |
| 2009/0131992 A1 | 5/2009 | Greenhalgh et al. | |
| 2010/0016905 A1 | 1/2010 | Greenhalgh et al. | |
| 2010/0100135 A1* | 4/2010 | Phan | 606/301 |
| 2010/0217325 A1* | 8/2010 | Hochschuler et al. | 606/264 |
| 2010/0228301 A1* | 9/2010 | Greenhalgh et al. | 606/313 |
| 2010/0303574 A1 | 12/2010 | McDuff et al. | |
| 2010/0324607 A1* | 12/2010 | Davis | 606/313 |
| 2011/0046682 A1 | 2/2011 | Stephan et al. | |
| 2011/0046737 A1 | 2/2011 | Teisen | |
| 2012/0109222 A1* | 5/2012 | Goel et al. | 606/310 |
| 2012/0184993 A1* | 7/2012 | Arambula et al. | 606/246 |
| 2012/0265258 A1* | 10/2012 | Garvey | 606/315 |

FOREIGN PATENT DOCUMENTS

| | | |
|---|---|---|
| EP | 0161916 | 11/1985 |
| EP | 277282 | 8/1988 |
| EP | 0322334 | 6/1989 |
| EP | 0480954 | 4/1992 |
| EP | 321020 | 10/1994 |
| EP | 0854198 | 7/1998 |
| FR | 2603256 | 3/1988 |
| FR | 2629337 | 10/1989 |
| FR | 2639823 | 6/1990 |
| FR | 2662073 | 11/1991 |
| FR | 2707477 | 1/1995 |
| FR | 2708192 | 2/1995 |
| FR | 2712486 | 5/1995 |
| FR | 2714590 | 7/1995 |
| FR | 2718634 | 10/1995 |
| FR | 2722679 | 1/1996 |
| FR | 2725892 | 4/1996 |
| FR | 2727304 | 5/1996 |
| FR | 2753080 | 3/1998 |
| FR | 2788082 | 11/1999 |
| FR | 2787313 | 6/2000 |
| FR | 2791551 | 10/2000 |
| FR | 2794019 | 12/2000 |
| FR | 2796846 | 2/2001 |
| FR | 2803532 | 7/2001 |
| FR | 2799117 | 4/2006 |
| GB | 2114005 | 8/1983 |
| RU | SU 1811865 | 4/1993 |
| RU | 2033755 | 4/1995 |
| RU | 2056797 | 3/1996 |
| RU | 2164152 | 3/2001 |
| RU | 2178681 | 1/2002 |
| SU | 906530 | 2/1982 |
| SU | 995751 | 2/1983 |
| WO | WO91/00713 | 1/1991 |
| WO | WO93/16664 | 9/1993 |
| WO | WO9420166 | 9/1994 |
| WO | WO9421320 | 9/1994 |
| WO | WO9856301 | 12/1998 |
| WO | WO9902108 | 1/1999 |
| WO | WO99/26554 | 6/1999 |
| WO | WO00/44319 | 8/2000 |
| WO | WO01/21246 | 9/2000 |
| WO | WO0128464 | 4/2001 |
| WO | 01/54598 | 8/2001 |
| WO | WO0176514 | 10/2001 |
| WO | 02/43628 | 6/2002 |
| WO | WO02/43628 | 6/2002 |
| WO | 03/007853 | 1/2003 |
| WO | WO2005/048856 | 6/2005 |
| WO | 2006/068682 | 6/2006 |
| WO | 2006/116760 | 11/2006 |
| WO | WO2006124764 | 11/2006 |
| WO | 2008/112308 | 9/2008 |
| WO | 2010/105174 | 9/2010 |
| WO | 2010/105196 | 9/2010 |

OTHER PUBLICATIONS

International Search Report and Written Opinion, dated Jun. 25, 2013, in connection with corresponding International Application No. PCT/US2013/028227.

U.S. Official Office Action, dated Jun. 15, 2011, in related U.S. Appl. No. 12/270,573.

U.S. Official Office Action, dated Sep. 20, 2012, in related U.S. Appl. No. 12/270,573.

Co-pending U.S. Appl. No. 12/270,573.

Official U.S. Office Action, mailed Sep. 20, 2012, received in connection with related U.S. Appl. No. 12/270,573.

Official U.S. Office Action, mailed Jun. 15, 2011, received in connection with related U.S. Appl. No. 12/270,573.

OsseoFix . . . The New Standard in VCF Treatment; OsseoFix Spinal Fracture Reduction System; Alphatec Spine, Inc.; www.alphatecspine.com (publication date not available).

* cited by examiner

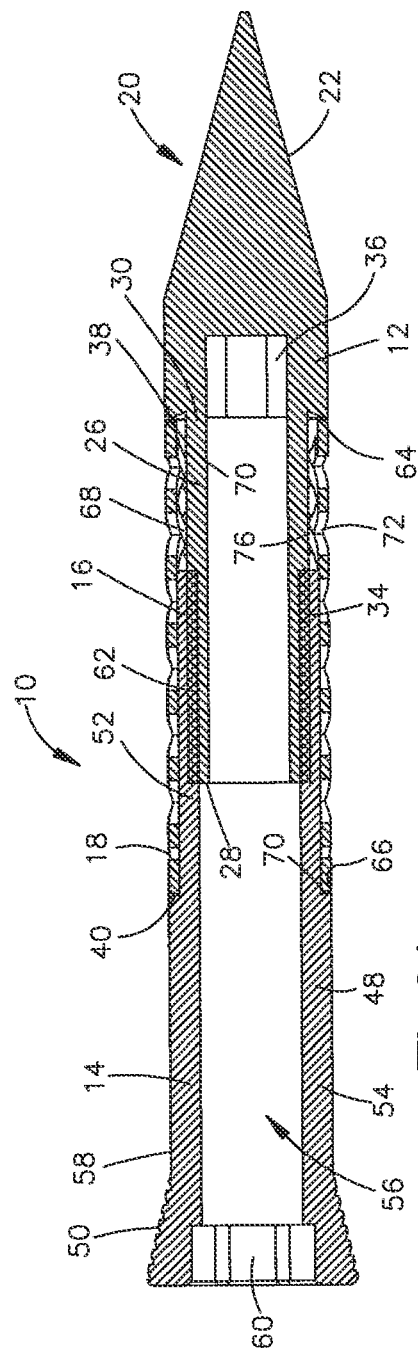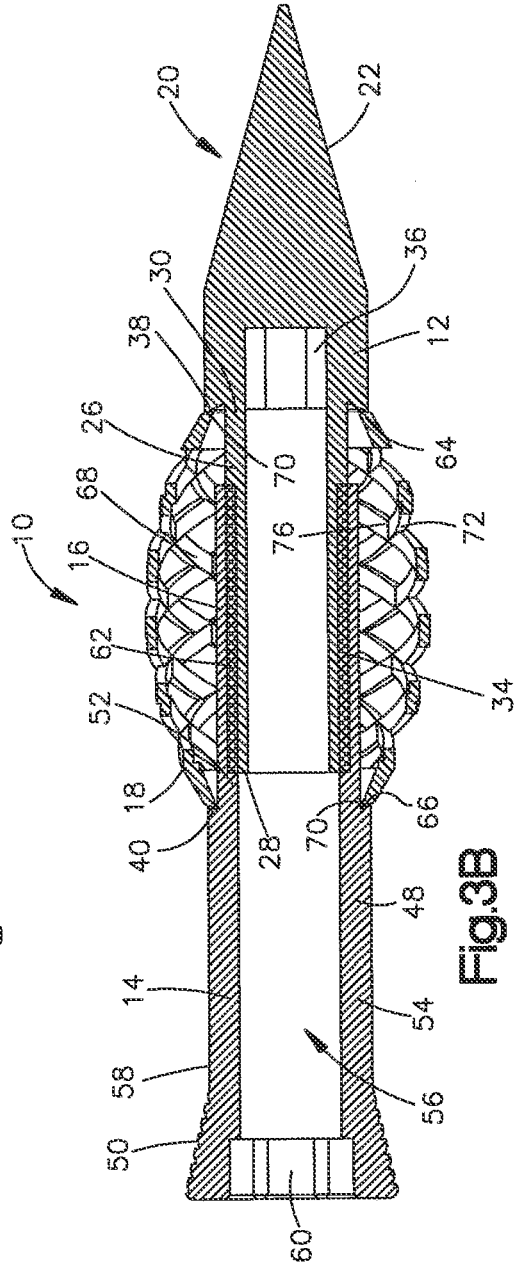

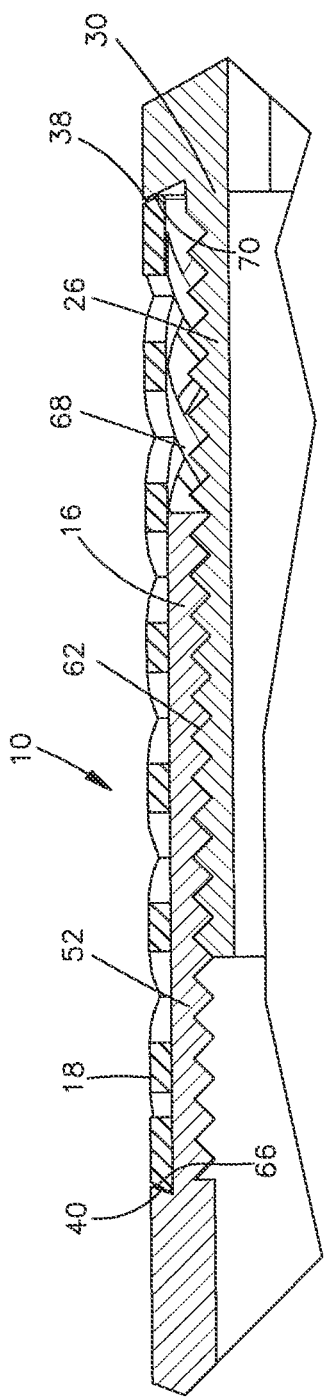
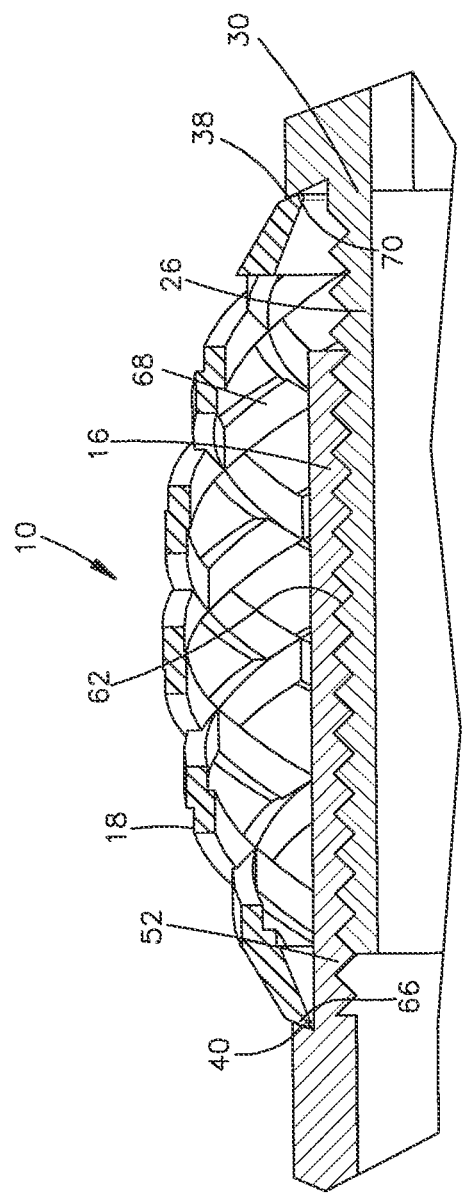

EXPANDABLE FASTENER

BACKGROUND

Achieving a firm fixation between the implants and the bony structure in case of osteoporotic bone remains a challenge.

For example, the current solution to treat degenerative disc disease and similar symptoms is with fusion. Generally, fusion requires implanting a spacer to restore disc height, lordosis and decompress neural structures. The spacer may either be fixed (held in place) from either a posterior, lateral or anterior direction with fixation elements. Thus, fixation is usually only from one side. A generally reliable fixation approach is a stand alone, anterior lumbar interbody fusion (ALIF) using a posterior fixation system that includes pedicle screws and rods.

Despite the effectiveness of the ALIF approach, improvements in fusion times are desired, especially for the aging spine.

SUMMARY

Implementations of the present disclosure overcome the problems of the prior art by providing a fastener including a tip portion, a proximal portion, an advancement mechanism and an expandable member. The tip portion has a first surface. The proximal portion is configured for coupling to the tip portion and has a second surface. The mechanism is configured to advance the first surface toward the second surface. The expandable member includes a first end abutting the first surface of the tip portion and a second end abutting the second surface of the proximal portion. Advancement of the two surfaces toward each other advances the first end of the expandable member toward the second end of the expandable member. The expandable member is configured to expand in response to the advancement. At least one of the ends of the expandable member is a free end extending under and configured to rotate with respect to an abutting one of the first or second surfaces.

At least one of the ends of the expandable member may have an angled face configured to congruently fit the abutting one of the surfaces. The angled face is configured to more congruently fit the abutting surface after rotation of the end.

The angled face may have an acute angle with respect to an axial direction of the fastener. For example, the acute angle may be 45 degrees. The abutting surface may also be an obtuse angle with respect to the axial direction.

An alpha angle of empty space may extend between the angled face and the abutting surface to provide room for rotation. For example, the alpha angle may be between 10 and 20 degrees before advancement of the first surface toward the second surface. The alpha angle may decrease to 0 degrees after advancement of the first surface toward the second surface due to rotation of the end having the angled surface.

Also, the expandable member may have an inner surface that is subjacent the angled surface. This inner surface may extend over an outer surface of the portion supporting the abutting surface. A clearance may extend between the inner surface and the outer surface. The clearance, for example, may be 5% or less of a diameter of the mechanism, such as 0.2 mm or less.

The inner surface may be on the first end of the expandable member and the outer surface on the tip portion. And, the first end may extend under the abutting surface of the tip portion. The first end may also have a rounded leading edge.

The mechanism may include threads of the tip portion engaging threads of the proximal portion. The tip portion and the proximal portion may also include a frictional engagement structure, such as external threads. The expandable member may also include a frictional engagement surface, such as a plurality of holes. For example, the expandable member may be a closed-cell stent with the cells defining the holes.

The expandable member may have a cylindrical shape and the ends may be tapered edges each defining an angled face extending therearound. The tip portion may also have a cylindrical portion with the first surface. Also, the proximal portion may include a cylindrical portion with the second surface. The first and second surfaces may be circular and angled toward an axis of the fastener. In this configuration, the tip and proximal portions may extend over the first and second ends (respectively) of the expandable member.

The expandable member is configured to expand at a ratio of diameter to contraction of 0.5:1 to 6:1.

In another configuration, the expandable member may have a locking portion that extends within a recess defined in one of the proximal or tip portions. The locking portion is circumferentially adjacent, through a cross-section, to one of the proximal or tip portions.

The locking portion, for example, may be a flange and the recess configured to congruently fit the flange. Multiple flanges and recesses may be used that extend circumferentially around the first and second ends. The flanges, for example, may be T-shaped flanges that have arms extending circumferentially.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

FIG. 3A is a cross-sectional view of the fastener of FIG. 1;

FIG. 3B is a cross-sectional view of the fastener of FIG. 2;

FIG. 10A is an enlarged cross-sectional view of the fastener of FIG. 1;

FIG. 10B is an enlarged cross-sectional view of the fastener of FIG. 2;

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Figure 1:
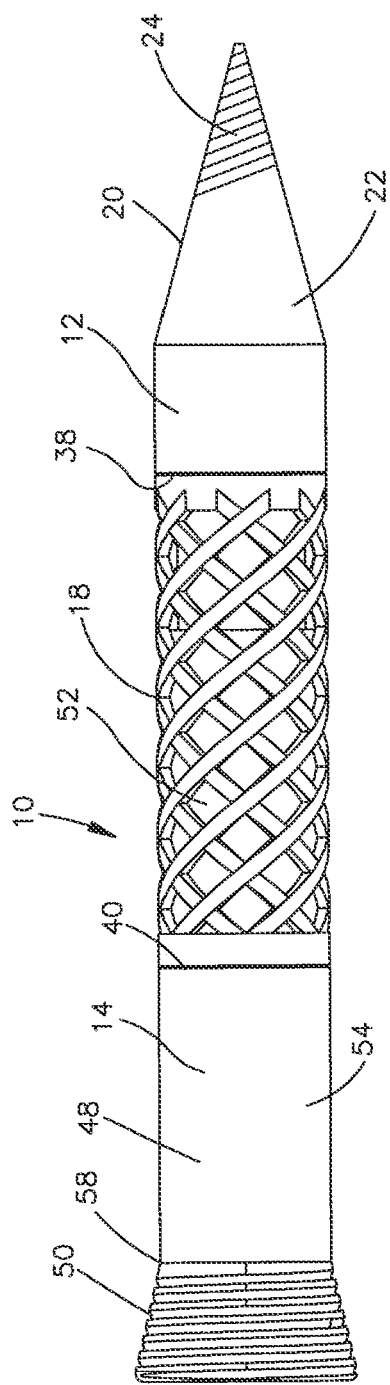
FIG. 1 is a side elevation view of a fastener with an expandable member.
Figure 2:
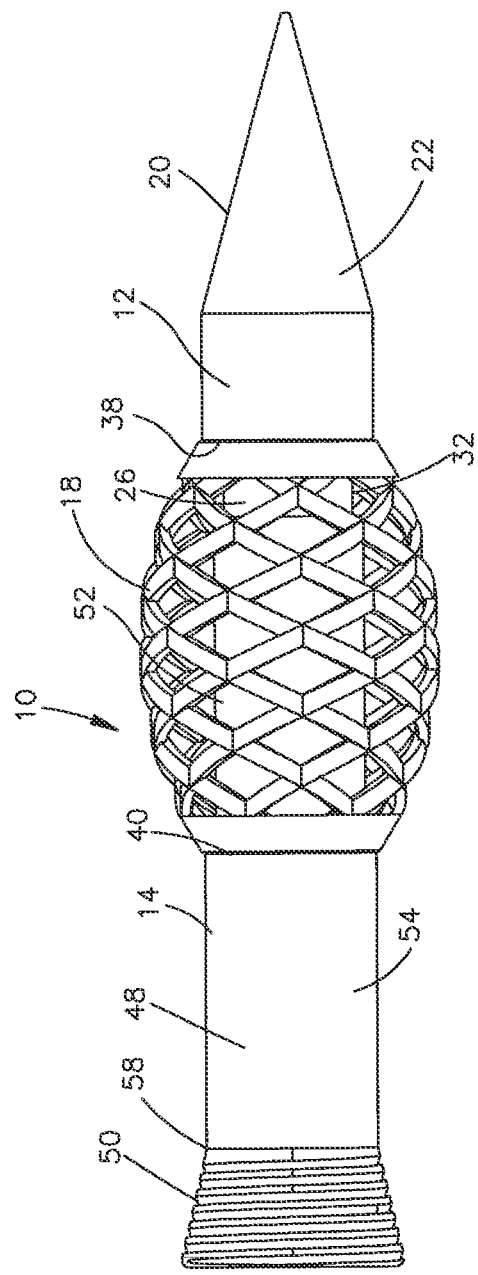
FIG. 2 is a side elevation view of the fastener of FIG. 1 with the expandable member in an expanded configuration.
Figure 4:
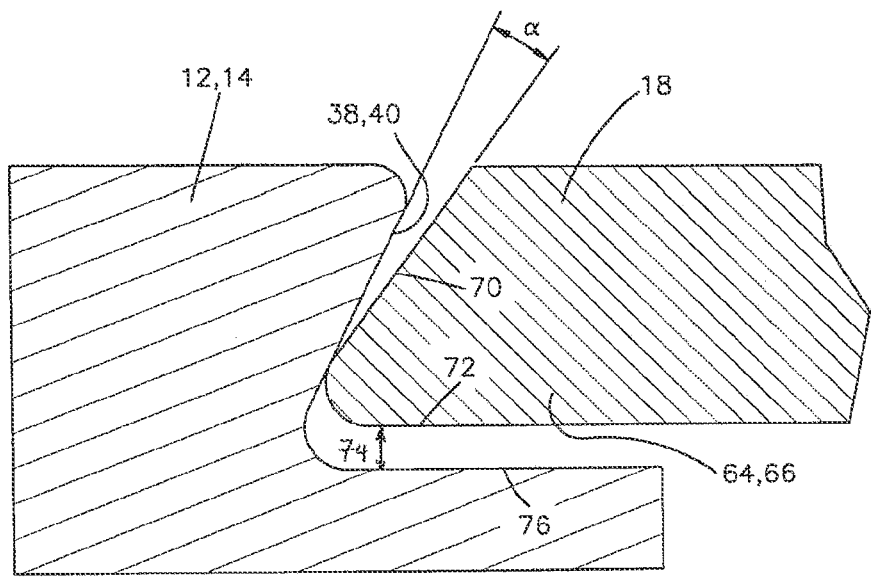
FIG. 4 is an enlarged schematic of a cross-section of an obtuse angled abutting surface abutting an acute angled surface at the end of an expandable member.
Figure 5:
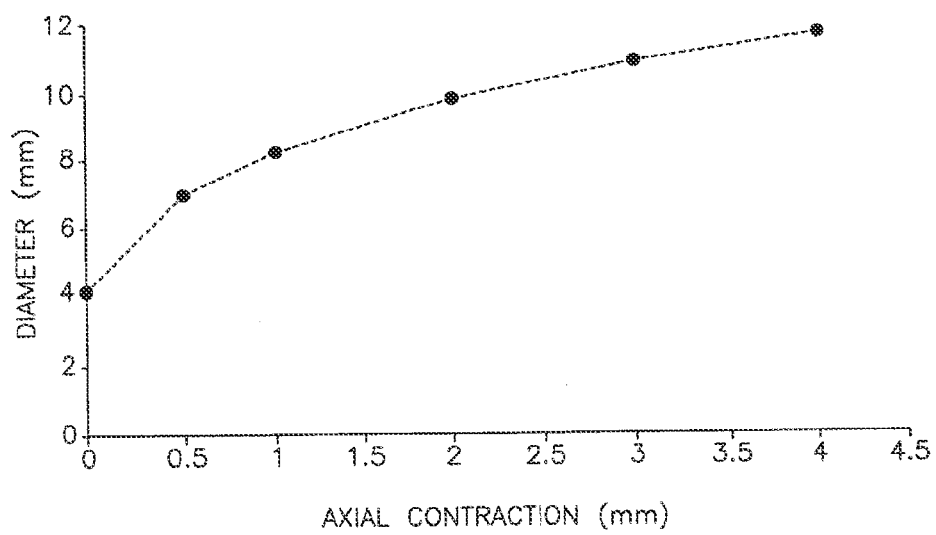
FIG. 5 is a graph of axial contraction versus diameter of the expandable member.
Figure 6:
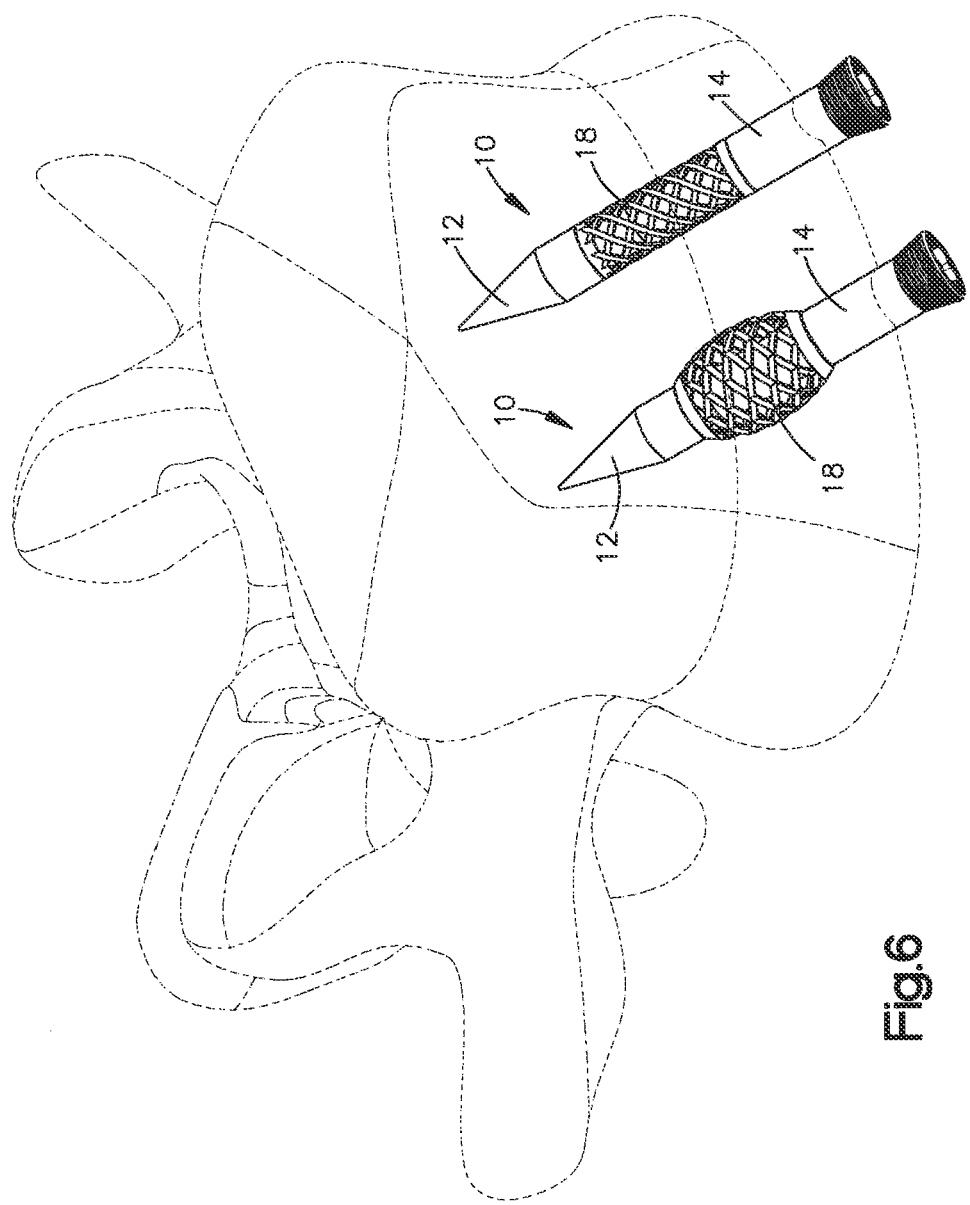
FIG. 6 is a perspective view of an expanded and unexpanded fastener of FIGS. 1 and 2 used in a vertebral bone fusion.

As shown in the accompanying FIGS. 1-11B, a fastener 10 includes a tip 12, a proximal portion 14 and a mechanism 16. The mechanism 16 is configured to urge the tip 12 and proximal portion 14 toward each other to axially compress and radially expand an expandable member 18, such as a stent, extending between the tip 12 and proximal portion 14. Expansion of the expandable member advantageously provides improved fixation of the fastener 10, such as within osteoporotic bone. FIG. 6, for example, shows an expanded fastener 10 and an unexpanded fastener 10 anchored into a vertebrae to cause or facilitate fusion.

FIGS. 1-3B show the tip 12 including a tapered end 20 and a shaft 26. The tapered end 20 may be configured for driving into a work piece, such as bone or other tissue during surgery. For example, the tapered end 20 is shown in FIGS. 3A and 3B as having a sharp point with a conical structure flaring proximally therefrom to form sloped surfaces 22. Preferably, the sloped surfaces have a frictional engagement structure, such as tip threads 24. The threads may be configured for hole initiation and expansion, such as by including helical threads. These threads serve to help anchor the distal end 20, and hence the tip 12 and the fastener 10.

The tapered end 20 is shown as having a conical structure, but could have other shapes configured to insert into bone or other work pieces. For example, a more blunt structure could be used rather than a pointed tip. An existing hole, for example, may be used in which case the distal end of the tip 12 may be cylindrical or semi-cylindrical or square with threads 24. Or, the end 20 could have no frictional engagement surface and instead merely provide a surface against which the expandable member 18 can be axially compressed. Also, the end 20 could have additional or alternative fixation structure or mechanisms, such as an expander that is spring loaded to fix in an existing cavity.

The shaft 26 includes a proximal end 28 and a distal end 32, as shown in FIGS. 3A and 3B. The distal end 30 of the shaft 26 is connected to tip 12 and extends in a proximal direction away from the tip 12. The shaft 26 is configured for driving of the tapered end 20 into the work piece and may also, as part of the mechanism 16, facilitate expansion of the expandable member 18. The shaft 26, for example, may be a cylindrical structure sharing a common axis with the tapered end 20 shown in FIGS. 3A and 3B. The shaft 26 may also include an outer surface and its own shaft threads 34 which are part of the mechanism 16.

The proximal end 28 or distal end 30 of the shaft may be configured to mate with a driver, such as by the use of a driving receptacle 36, shown in FIGS. 3A and 3B. The driving receptacle 36 may have a non-round cross-section, such as a square or hexagonal or hexalobular cross-section, configured to mate with and be driven by the tip of a driver.

Adjacent the distal end 30 of the shaft is a first abutting surface 38 that is configured to abut with the expandable member 18 as will be described in more detail below. The first abutting surface 38 shown in FIGS. 3A and 3B is a circular chamfer on the tapered end 20 that is angled toward the axis of the shaft 26.

The proximal portion 14 of the fastener includes a sleeve 48 at its distal end and a head 50 at its proximal end and defines an axial bore 56. The sleeve 48 has a generally cylindrical shape that extends along the longitudinal axis of the fastener 10. The sleeve 48 includes a first sleeve portion 52, a second sleeve portion 54 and a neck 58. The first sleeve portion 52 is at the distal end of the sleeve 48 opposite the head 50. The first sleeve portion 52 has an outer cylindrical surface that is configured to extend under the expandable member 18, as shown in FIGS. 3A and 3B. Also, the first sleeve portion 52 has a first diameter.

The second sleeve portion 54 is at the proximal end of the sleeve 48. The second sleeve portion 54 has a second diameter that is larger than the first diameter of the first sleeve portion 52. An outer surface of the second sleeve portion 54 may define a frictional engagement structure, such as threads or knurls. The frictional engagement structure may facilitate securing of the fastener 10 into the bone or other work piece.

The threads on the outer surfaces of the fasteners 10 may be selected to promote compression or distraction of the surrounding bone. For example, the head 50 second sleeve portion 54 may include threads that are at a greater pitch than the threads of the tip 12 or first sleeve portion 52. In this instance, each turn of a driver would cause the proximal portions of the fastener to advance further into the bone than the distal portions. This would compress two or more bone fragments of a comminuted fracture together.

Also, different thread directions could be used on the head 50 or second sleeve portion 54 from those on the tip 12 or first sleeve portion 52. Each turn of the driver would drive the differently threaded portions either toward or away from each other.

Also note that the fastener 10 may be fully or partially driven into the bone or other tissues by direct hammering. Or a combination of hammering and rotational driving could be employed. For example, the distal end of the fastener 10 could be fixed by hammering and the head 50 or second sleeve 54 rotated clockwise or counterclockwise to compress or distract two adjacent bone portions.

The transition between the first and second diameters 52, 54 forms a second abutting surface 40. As shown in FIGS. 3A and 3B, the second abutting surface 40 is a circular chamfer that is angled toward the axis of the proximal portion 14. In the illustrated configuration, the circular chamfers of the first and second abutting surfaces 38, 40 are spaced apart from and mirror each other. They have the same size and shape, except that they're angled in different directions to hold ends of the expandable member 18 therebetween.

Figure 7:
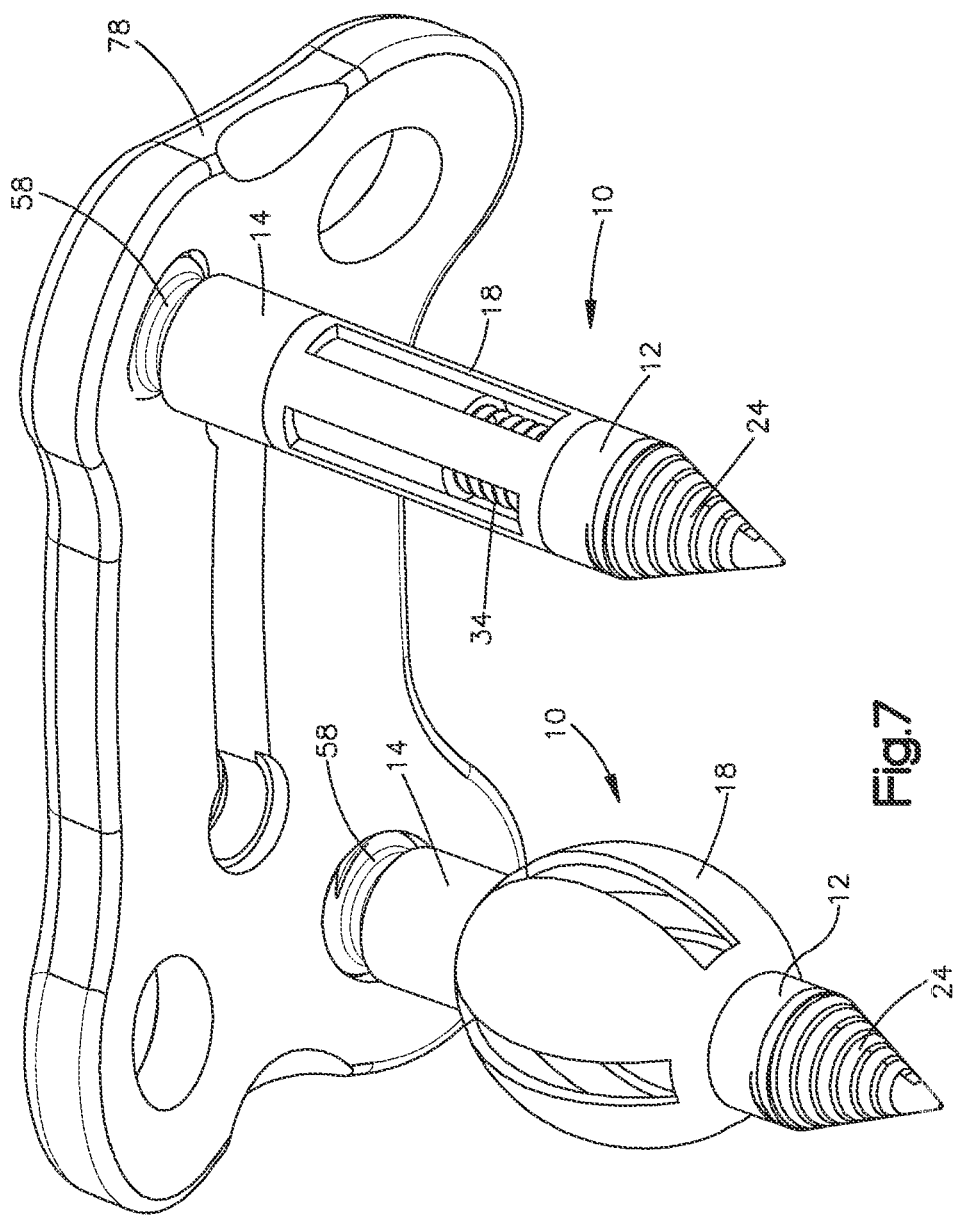
FIG. 7 a perspective view of a bone plate being secured with fasteners having expandable members.

The neck 58, as shown in FIGS. 1-3B, is a transition point between the sleeve 48 and the head. Optionally, the neck 58 may include, as shown in FIG. 7, a diameter reduction proximal of the second sleeve portion 54 that transitions to attachment of the head 50. In this configuration, the neck has a diameter slightly larger than a diameter of the first sleeve portion 52.

The head 50 has a frusto-conical shape that flares as it extends in the proximal direction. The head 50 may also include an outer frictional engagement surface, such as threads, for additional security within the bone or other work piece. The flared shape of the head 50 may help to arrest its advancement into the bone and to more tightly secure the fastener 10. The head 50 need not have a larger diameter than the rest of, or even need be used in, the fastener 10, depending upon the application. For example, if the fastener 10 were to be used to secure an anterior cruciate ligament graft by deep insertion into a bone tunnel, the head 50 may have the same diameter as the rest of the proximal portion 14.

The head 50 defines a driving receptacle 60, similar to the driving receptacle 36 of the shaft 26 except that it has a larger diameter. The driving receptacle 60 is configured to receive a driver that has an axial opening allowing the driver to be sleeved over a smaller driver that extends down the bore 56. The outer, larger driver and inner, smaller driver can thus differentially drive the tip 12 and the proximal portion 14, as will be described in more detail below.

The bore 56 extends distally from the driving receptacle 60 and is defined by the sleeve 48, neck 58 and a portion of the head 50 not defining the driving receptacle 60. Generally, the bore 56 has a cylindrical shape configured to pass the inner, smaller driver shaft. Defined within a distal portion of the bore 56 are cylindrically extending bore threads 62. The bore threads 62 are configured to externally engage the shaft threads 34 and form part of the mechanism 16.

The expandable member 18 is a structure configured to radially expand when axially compressed by the mechanism 16. For example, as shown in FIGS. 1-3A, the expandable member 18 includes a stent with a first stent end 64 and a second stent end 66. The stent 18 has a crisscross wire construction that forms a plurality of closed cells in between a solid cylindrical portion at the first stent end 64 and the second stent end 66. The stent 18 has a cylindrical shape and defines an axial lumen 68 extending its length.

The expandable member 18 may have other expandable structure, such as a slotted tube with a bone-engaging outer surface that expands radially with axial compression, as shown in FIG. 7.

Although other expandable member 18 structures are possible, use of a monolithic stent has some advantages. It lowers the number of components that could fall apart. It may have thinner geometric features, facilitating a smaller outside diameter, inside diameter and weight. Also, use of monolithic stent reduces the number of components to be manufactured.

Also, the stent may have dozens of expanding elements/cells that allow the stent to expand in a controlled homogenous fashion versus, for example, a hinged structure that consists of only one single cell. Such a single cell results in a diamond-shaped aperture.

Stents may be made from a high-strength plastically (irreversibly) deformable material, such as CoCr or 316L. This helps keep the expanded stent from inadvertently reverting (collapsing) back to its original (un-deformed) shape or configuration. Hinged structures are more prone to collapse after expansion because the hinge is the weakest link.

Further, the fully expanded stent creates a large surface area of contact with the cancellous bone. A more hinged structure, on the other hand, creates a point contact prone to leading to subsidence into the disc space.

In addition, the fully expanded stent creates a large surface area contact with the cancellous bone. This leads to higher pull-out forces and better anchoring, whereas the hinged structure creates a smaller surface area potentially leading to screw pull-out.

Although shown positioned in the middle of the fastener 10, the expandable member 18 could be enlarged relative to the tip 12 and proximal 14 portions. Also, the expandable member 18 could be shifted proximally or distally along the fastener 10 as long as two relatively (i.e., at least one movable) surfaces are supplied to compress the ends of the expandable member 18. The expandable member 18, for example, could be at the very tip of the fastener 10.

The first stent end 64 and second stent end 66 may each have an angled face. For example, the ends may have a bevel, such as a circular bevel, extending around the expandable member 18. The circular bevel may be at an acute angle with respect to an axial direction of the fastener 10, such as 45 degrees. The abutting surfaces 38, 40 may also have an obtuse angle with respect to the axial direction. Also, the stent ends 64 and 66 may have a rounded outermost edge.

The shape of the abutting surfaces 38, 40 engaging the beveled face help to restrain the expandable member 18 against slipping off of the tip 12 and proximal portion 14, as shown in FIGS. 10A and 10B. Different angles and shapes could be used to modify the path of the ends of the stent or other expandable member 18 and the concomitant expansion shape of the expandable member. For example, the abutting surfaces 38, 40 may have an additional rounded shape applied to the bevel so as to promote a quicker expansion in between a start and stop of an application of compression by the mechanism 16. From one perspective, the varied shapes of the compressing faces on the tip 12 and proximal portion 14 and the abutting surfaces 38, 40 allow for a controlled cam action that dictates the rate and shape of expansion of the expandable member 18.

As shown in FIG. 4, an alpha angle ($\alpha$) of empty space may extend between the beveled face 70 and the abutting surface 38 or 40 when the fastener 10 is in an unexpanded configuration. The alpha angle provides room for easier initial rotation of the beveled face 70 relative to the abutting surface. This rotation allows for a more aggressive expansion of the expandable member. At the same time, the congruency of the abutting surfaces secures the free rotating ends against slipping off of the rest of the structure of the fastener 10.

For example, the alpha angle may be between 10 and 20 degrees before the congruent contact slows further rotation of the stent ends 64, 66. Thus, due to rotation of the stent end 64 or 66 relative to the compressing beveled face(s) 70, the alpha angle decreases to 0 degrees after sufficient advancement of the first surface 38 toward the second surface 40. The congruent contact could then shift further expansion from the ends of the stent more to the middle.

Similar to the shape of the intersecting surfaces, the alpha angle can be selected to program the expansion characteristics of the expandable member 18. Changing the alpha angle changes the amount of rotation before the face and abutting surfaces meet in congruent contact. Advantageously, the congruent contact of the ends 64, 66 and the faces 70 restrains the stent or other expandable member 18 from disengaging the tip 12 and/or proximal portion 14 and losing its expansion or anchoring function.

As shown by FIG. 4, the expandable member 18 may have an inner surface 72 that is subjacent the beveled face 70. This inner surface 72 extends over an outer surface 76 of the tip 12 or proximal portion 14. A clearance 74 may extend between the inner surface and the outer surface. The clearance 74 provides further room for rotation of the stent ends 64, 66 relative to the tip 12 or proximal portion 14. The clearance 74, for example, may be 5% or less of a diameter of the mechanism, such as 0.2 mm or less. As noted above, advantages of this configuration are facilitating rotation of the free ends of the expandable member 18 for more aggressive expansion. Also, at the same time, the ends of the expandable member are retained by the tip 12 and proximal portion 14.

The mechanism 16, as mentioned above, may be comprised of parts of the other components of the fastener 12. Functionally, the mechanism 16 is configured to advance the two ends 64, 66 of an expandable member 18 toward each other so as to cause its expansion. In the illustrated configuration, this is accomplished by differential driving of the tip 12 relative to the proximal portion. For example, a larger, outer driver is used to engage driving receptacle 60 and a smaller, inner driver extends through the outer driver to engage driving receptacle 36. Relative rotation of the proximal portion 14 advances the bore threads 62 along the shaft threads 34, moving the first and second butting surfaces 38 and 40 toward each other and compressing the ends 64, 66.

The mechanism 16 may have other function and structure for advancing the two ends 64, 66 toward each other. A ratcheting mechanism, for example, could be used to advance the two ends together. The ratcheting mechanism could be manually actuated or driven by a motor, for example.

As noted above, the fastener 10 is configured to allow its expandable member 18 to have rotatable ends. The rotatable ends generate a desired expansion shape that can be characterized by the following equations.

The length of the expandable is reduced due to contraction caused by the screw threads and therefore L can be calculated as follows:

$$L = L_0 - N \times P \quad (1)$$

The total length of the expandable stays the same:

$$R\Theta = L_0 \quad (2)$$

The trigonometric relation in the triangle (OAB) requires:

$$2R\sin\left(\frac{\Theta}{2}\right) = L \quad (3)$$

A comparison of (1) and (3) results in:

$$\frac{\Theta}{\sin\left(\frac{\Theta}{2}\right)} = \frac{2L_0}{L} \quad (4)$$

In equation (4) the angle is the only unknown and can be calculated as the root of the equation. As theta is calculated, the radius (R) can also be calculated:

$$R = \frac{L_0}{\Theta} \quad (5)$$

Using the geometry of the triangle (OAB) again, the new diameter can be calculated $$D = D_0 + 2R\left(1 - \cos\left(\frac{\Theta}{2}\right)\right) \quad (6)$$

Figure 11A:
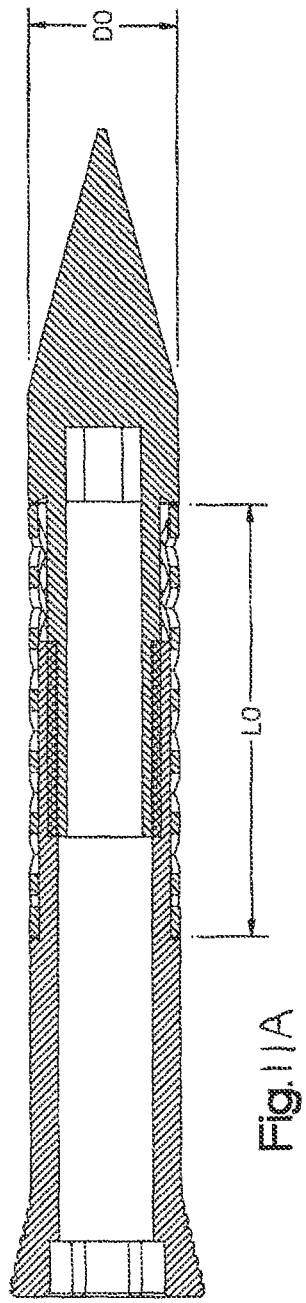
FIG. 11A is a cross-sectional view of the fastener of FIG. 1 showing variables defining geometric relationships for expansion.
Figure 11B:
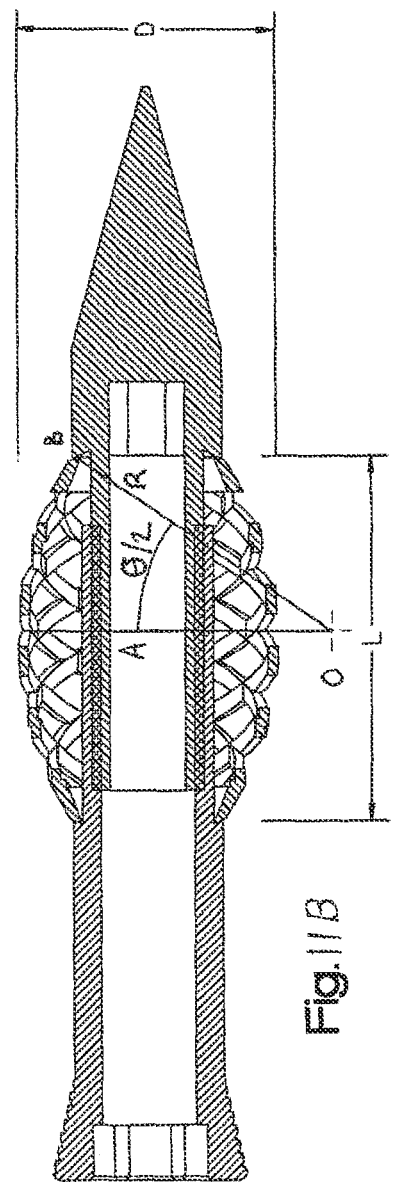
FIG. 11B is a cross-sectional view of the fastener of FIG. 2 showing variables defining geometric relationships for expansion.

Parameters, some of which are shown in FIGS. 11A and 11B:
$L_0$: Initial length of the expandable (known)
$D_0$: Initial diameter of the expandable (known)
N: number of turns on internal screw (known)
P: Pitch on the threads of the internal screw (known)
L: Current length (in expanded form) of the expandable (unknown)
D: Current diameter (in expanded form) of the expandable (unknown)
R: Curvature radius in deformed state (unknown)
$\Theta$: Curvature total angle (unknown)

FIG. 5 shows a graph of a resulting expansion of the expandable member 18 with its ends rotating during compression and with $L_0 = 12$ mm and $D_0 = 4$ mm. Notably, the ratio of the diameter expansion of the expandable member 18 to its contraction ranges from about 0.5:1 to 6:1, depending upon the stage of expansion. Expansion is higher with relative contraction earlier on the curve, i.e., 6:1 ratio of expansion to contract initially, and then drops off with further contraction.

During use, the surgeon hammers or drives the fastener 10 into the bone so as to secure the tip 12. The external threads on the tip 12 may be relatively high pitch to allow for linear insertion and to offer friction for anchoring and bone ingrowth. The proximal portion 14 is then rotated relative to the tip 12 and the expandable member 18 is expanded as explained above. The amount of radial expansion is a function of the amount of contraction between the tip 12 and proximal portion 14. The external threads (such as an LCP thread) on the outside of the proximal portion 14 can be positioned within the disc space, as shown in FIG. 6. The threads on the proximal portion 14 can be used to attach the fastener 10 to an intervertebral cage.

The fastener 10 has several advantages for improving the security of fixation. It can supply three fixed supporting points, for example, such as the LCP threads on the tip 12, cortical threads on the proximal portion 14 and the expandable member 18 in between. Conventional devices, in comparison, rely on anterior anchoring. The fastener 10 distributes the load more equally by supplying a posterior fixation for an ALIF approach. Better force distribution reduces static and dynamic bending moments on the fastener 10. Also, the fastener 10's distribution of load allows anchoring in osteoporotic or cancellous bone.

The fastener 10 may also provide an anterior approach to treating spondylolisthesis. Spondylolisthesis has its origins at the posterior structures where the fastener 10 provides improved anchoring. The fastener 10 could also have benefits or uses for other approaches, including posterior, lateral, antero-lateral (oblique), extra-foraminal, trans-foraminal and anterior fixation elements. The fastener 10 could also be employed in place of conventional pedicle screws, such as with plates and rods.

As shown in FIG. 7, the fastener 10 may be used with an anterior tension band (ATB) plate 80. Advantageously, the ATB plate 80 can be removed or revised by removing the proximal portion 14 of the fastener 10.

The fastener 10's ability to be anchored proximally and distally may be used for attaching two bones (bi-segmental) to each other. Thus, the fastener 10 could be used for single or multi-level fixation. For example, the fastener 10 may be used to fuse adjacent vertebrae in the cervical, thoracic or lumbar spine.

Materials used for the fastener 10's components include biocompatible materials such as titanium and its alloys (e.g. TAN, TAV), stainless steel, cobalt-chrome alloys, polymers (e.g. PEEK, UHMWPE), ceramics and biodegradable materials. Coatings could also be employed such as physical vapor deposition (PVD), chemical vapor deposition (CVD), plasma assisted chemical vapor deposition (PACVD), chemical vapor aluminizing (CVA) and diamond-like carbon (DLC).

Figure 8:
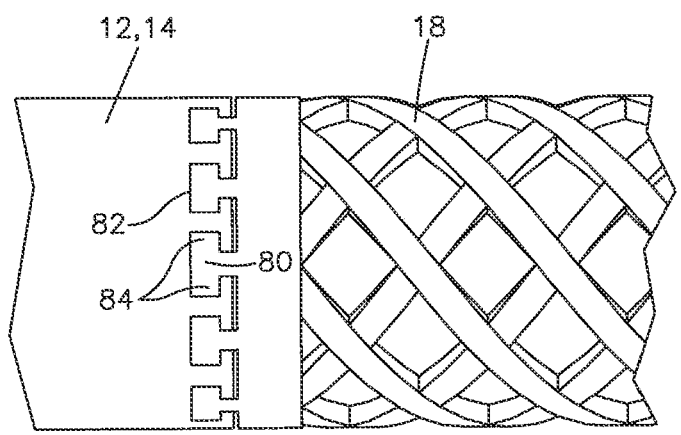
FIG. 8 is schematic of a locking portion securing an end of an expandable member to a fastener shaft.

As shown in FIG. 8, the expandable member 18 may have a locking portion 80 that extends within a recess 82 defined in one of the proximal or tip portions 14, 12.

The locking portion 80, for example, may include a flange and the recess 82 configured to congruently fit the flange. The locking portion 80 is circumferentially adjacent, through a cross-section, to one of the proximal or tip portions. Multiple flanges and recesses may be used that extend circumferentially around the first and second ends. The flanges, for example, may be T-shaped flanges that have arms 84 extending circumferentially.

Figure 9:
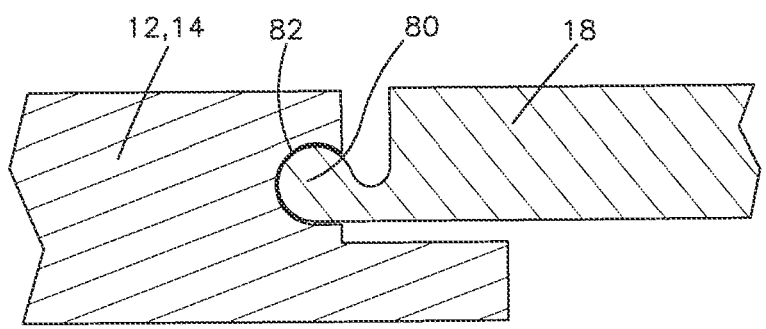
FIG. 9 is a schematic of a cross-section of another locking portion securing an expandable member end to a fastener shaft.

FIG. 9 shows another variation wherein the locking portion 80 has a rounded tip that extends into a rounded recess 82. The rounded tip may provide for relative rotation of the stent ends 64, 66 while at the same time locking against slippage of the expandable member 18 off of the proximal portion 14 and tip portion 12. An additional band or ring may be secured about the interdigitated locking portions and recesses for additional security.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A fastener comprising:
   a tip portion having a first surface;
   a proximal portion configured for coupling to the tip portion and having a second surface;
   a mechanism configured to advance the first surface toward the second surface; and
   an expandable member having a first end abutting the first surface of the tip portion and a second end abutting the second surface of the proximal portion;
   wherein the first surface includes an angled face extending from an outer surface of the tip portion towards a longitudinal axis of the fastener in a direction towards a distal end of the tip portion, the first end including a corresponding angled face,
   wherein the second surface includes an angled face extending from an outer surface of the proximal portion towards a longitudinal axis of the fastener in a direction towards a proximal end of the proximal portion, the second end including a corresponding angled face,
   wherein advancement of the first surface toward the second surface advances the first end of the expandable member toward the second end of the expandable member,
   wherein the expandable member is comprised of crisscross wires, and is configured to radially expand in response to advancement of the first end toward the second end,
   wherein at least one of the ends of the expandable member is a free end extending between an abutting one of the first or second surfaces and the longitudinal axis of the fastener, the at least one end of the expandable member configured to rotate with respect to the abutting one of the first or second surfaces.

2. A fastener of claim 1, wherein the angled face of each of the first and second ends are configured to congruently fit the corresponding first and second surface.

3. A fastener of claim 2, wherein the angled face of each of the first and second ends is configured to more congruently fit the corresponding abutting surface after rotation of the expandable member.

4. A fastener of claim 3, wherein the angled face has an acute angle with respect to an axial direction.

5. A fastener of claim 4, wherein the acute angle is between 30 and 60 degrees.

6. A fastener of claim 5, wherein the acute angle is 45 degrees.

7. A fastener of claim 4, wherein the abutting surface has an obtuse angle with respect to the axial direction.

8. A fastener of claim 7, wherein an alpha angle of empty space extends between the angled face and the abutting surface, the alpha angle measured between the abutting surface and the angled face in a direction along the longitudinal axis of the fastener.

9. A fastener of claim 8, wherein the alpha angle is between 10 and 20 degrees before advancement of the first surface toward the second surface.

10. A fastener of claim 9, wherein the alpha angle decreases to 0 degrees after advancement of the first surface toward the second surface due to rotation of the end having the angled surface.

11. A fastener of claim 10, wherein the expandable member has an inner surface subjacent the angled face.

12. A fastener of claim 11, wherein the inner surface of the expandable member extends over an outer surface of the portion supporting the abutting surface.

13. A fastener of claim 12, wherein a clearance extends between the inner surface of the expandable member and the outer surface of the portion.

14. A fastener of claim 13, wherein the clearance is 5% or less of a diameter of the mechanism.

15. A fastener of claim 14, wherein the clearance is 0.2 mm or less.

16. A fastener of claim 1, wherein the expandable member has an inner surface and an outer surface and a clearance extends between the inner surface and the outer surface.

17. A fastener of claim 16, wherein the clearance is 5% or less of a diameter of the mechanism.

18. A fastener of claim 17, wherein the clearance is 0.2 mm or less.

19. A fastener of claim 17, wherein the inner surface is on the first end of the expandable member and the outer surface is on the tip portion.

20. A fastener of claim 19, wherein the first end extends between the first surface of the tip portion and the longitudinal axis of the fastener.

21. A fastener of claim 20, wherein the first end has a rounded leading edge.

22. A fastener of claim 1, wherein the mechanism includes threads of the tip portion engaging threads of the proximal portion.

23. A fastener of claim 22, wherein the tip portion and proximal portion include a frictional engagement structure.

24. A fastener of claim 23, wherein frictional engagement structure of the tip portion and proximal portion are threads.

25. A fastener of claim 24, wherein the expandable member includes a frictional engagement surface.

26. A fastener of claim 25, wherein the frictional engagement surface of the expandable member includes a plurality of holes.

27. A fastener of claim 26, wherein the expandable member is a stent.

28. A fastener of claim 27, wherein the stent is a closed-cell stent.

29. A fastener of claim 1, wherein the expandable member has a cylindrical shape and the at least one of the ends has a tapered edge defining an angled face extending therearound.

30. A fastener of claim 29, wherein each of the first and second ends of the expandable member has the tapered edge.

31. A fastener of claim 30, wherein the tip portion includes a cylindrical portion with the first surface and the proximal portion includes a cylindrical portion with the second surface.

32. A fastener of claim 31, wherein the first and second surfaces are circular and angled toward an axis of the fastener.

33. A fastener of claim 32, wherein the tip and proximal portions extend over the first and second ends of the expandable member.

34. A fastener of claim 1, wherein the expandable member is configured to expand at a ratio of diameter to axial contraction between 0.5:1 and 6:1.

35. A fastener of claim 1, wherein the tip portion has a first plurality of threads and the proximal portion has a second plurality of threads.

36. A fastener of claim 1, wherein the fastener further comprises a locking portion located on at least one of the first and second ends of the expandable member, the locking portion including a projection extending from the least one of the first and second ends engaging a corresponding recess provided in the corresponding tip and proximal portions such that the locking portion secures the end of the expandable member to the corresponding tip proximal portions.

37. A fastener comprising:
   a tip portion having a first surface;
   a proximal portion configured for coupling to the tip portion and having a second surface;
   a mechanism configured to advance the first surface toward the second surface; and
   an expandable member having a first end abutting the first surface of the tip portion and a second end abutting the second surface of the proximal portion;
   wherein the first surface includes an angled face extending from an outer surface of the tip portion towards a longitudinal axis of the fastener in a direction towards a distal end of the tip portion, the first end including a corresponding angled face,
   wherein the second surface includes an angled face extending from an outer surface of the proximal portion towards a longitudinal axis of the fastener in a direction towards a proximal end of the proximal portion, the second end including a corresponding angled face,
   wherein advancement of the first surface toward the second surface advances the first end of the expandable member toward the second end of the expandable member,
   wherein the expandable member is comprised of crisscross wires, and is configured to radially expand in response to advancement of the first end toward the second end and wherein the expandable member is configured to expand at a ratio of diameter to axial contraction between 0.5:1 and 6:1.

38. A fastener of claim 37, wherein the fastener further comprises a locking portion located on at least one of the first and second ends of the expandable member, the locking portion including a projection extending from the least one of the first and second ends engaging a corresponding recess provided in the corresponding tip and proximal portions such that the locking portion secures the end of the expandable member to the corresponding tip and proximal portions.

* * * * *